(12) United States Patent
Friedman

(10) Patent No.: US 6,713,306 B1
(45) Date of Patent: Mar. 30, 2004

(54) METHOD FOR IDENTIFICATION OF FLUNITRAZEPAM

(75) Inventor: Arthur J. Friedman, Deerfield, IL (US)

(73) Assignee: R. E. Davis Chemical Corporation, Oak Brook, IL (US)

( * ) Notice: Subject to any disclaimer, the term of this patent is extended or adjusted under 35 U.S.C. 154(b) by 405 days.

(21) Appl. No.: 09/946,225

(22) Filed: Sep. 5, 2001

(51) Int. Cl.⁷ .............................................. G01N 33/00
(52) U.S. Cl. ...................... 436/96; 436/106; 436/164; 436/815; 436/901
(58) Field of Search .......................... 436/96, 106, 164, 436/815, 901

(56) References Cited

U.S. PATENT DOCUMENTS

| | | |
|---|---|---|
| 4,752,448 A | 6/1988 | Wells et al. |
| 4,844,866 A | 7/1989 | Wallace et al. |
| 4,981,786 A | 1/1991 | Dafforn et al. |
| 4,992,296 A | 2/1991 | Gibson |
| 5,457,054 A | 10/1995 | Geisinger et al. |
| 6,153,147 A | 11/2000 | Craig |

OTHER PUBLICATIONS

"Rapid testing method and mechanism of the reaction with 4–dimethylamino–cinnamaldehyde (DMAC); coloured salts of benzodiazepines–part III"; M. Laudszun, K.A. Kovar; Pharm. Acta Helv. 66. Hr. 9–10 (1991) pp 268–273.

*Primary Examiner*—Jill Warden
*Assistant Examiner*—Monique T. Cole
(74) *Attorney, Agent, or Firm*—Godfrey & Kahn, S.C.

(57) ABSTRACT

A method for detecting the presence of flunitrazepam in a sample. Flunitrazepam contained within the sample is reduced and hydrolyzed by the addition of a hydrolyzing agent and a reducing agent. A visualizing agent is provided to combine with the reduced and hydrolyzed species corresponding to the flunitrazepam to yield a colored species providing a qualitative colorimetric indication of the presence of flunitrazepam within the sample. The invention is a rugged and dependable method suitable for use in the field.

31 Claims, No Drawings

METHOD FOR IDENTIFICATION OF FLUNITRAZEPAM

BACKGROUND OF THE INVENTION

The present invention is concerned with a method for identification of a date rape drug. Specifically, the invention is a method for the qualitative identification of flunitrazepam in a sample such as a beverage.

Flunitrazepam is a member of the benzodiazepine class of drugs and is marketed under the brand name ROHYPNOL. Flunitrazepam has never been approved for medical use in the United States, therefore, doctors cannot prescribe it and pharmacists cannot sell it. However, it is legally prescribed in over 50 other countries and it is widely available in Mexico, Colombia, and Europe where it is used in the treatment of insomnia and as a pre-anesthetic. Unfortunately, flunitrazepam has become a popular illicit drug in the United States and is commonly known in the illegal drug trade as roofies, roach, or rope.

Like other benzodiazepines (such as those distributed under the brand names VALIUM, LIBRIUM, XANAX and HALCION), flunitrazepam's pharmacological effects include sedation, muscle relaxation, reduction in anxiety and prevention of convulsions. However, flunitrazepam's sedative effects are approximately 7 to 10 times more potent than diazepam (VALIUM). The effects of flunitrazepam appear approximately 15 to 20 minutes after administration and last approximately 4 to 6 hours. Some residual effects can be found 12 hours or more after administration.

Flunitrazepam causes partial amnesia; individuals are often unable to remember certain events that they experience while under the influence of the drug. This effect is particularly dangerous when flunitrazepam is used to aid in the commission of sexual assault. Victims may not be able to clearly recall the assault, the assailant, or the events surrounding the assault. It is difficult to estimate how many flunitrazepam-facilitated rapes have occurred in the United States. This problem is the direct result of the amnesia induced by the drug which causes the victim to be uncertain about the facts surrounding the rape. This uncertainty may lead to critical delays or a reluctance to report the rape and provide appropriate biological samples for use in apprehending the assailant.

Flunitrazepam abuse causes a number of adverse effects in the abuser, including drowsiness, dizziness, loss of motor control, lack of coordination, slurred speech, confusion, and gastrointestinal disturbances, lasting 12 or more hours. Higher doses produce respiratory depression. Chronic use of flunitrazepam can result in physical dependence and the appearance of withdrawal syndrome when the drug is discontinued. Flunitrazepam is known to impair cognitive and psychomotor functions affecting reaction time and therefore driving skills. The use of this drug in combination with alcohol is a particular concern as both substances appear to potentiate each other's toxicity.

To avoid being the victim of an flunitrazepam-induced assault, both men and women are commonly advised to never accept an open drink at a social event, particularly from a stranger. In addition, it is advisable for individuals to ask for beverages available in sealed containers and to insist upon opening the beverage themselves. Because flunitrazepam is colorless, ordorless and tasteless when dissolved in beverages it is very difficult to detect if a beverage has been spiked with the drug. Therefore, it is desirable to provide a simple, low cost and reliable method to avoid the insidious, disgusting and perilous dangers of suffering an unwanted flunitrazepam-related high or trip induced by a potential assailant slipping flunitrazepam into an unguarded beverage. Such a method would also be useful to law enforcement or medical personnel desiring a simple, rugged field test for the presence of flunitrazepam at crime scenes.

SUMMARY OF THE INVENTION

The present invention is an improvement on previous methods for the qualitative determination of flunitrazepam in a sample. In general, the method is initiated by obtaining a sample suspected to contain flunitrazepam. The sample may come from a beverage handed to a partygoer by a stranger. This beverage may contain ethanol in addition to flunitrazepam. If there is concern as to the safety of the beverage, an individual may use the present invention to detect whether or not the beverage was spiked with flunitrazepam.

According to the invention, flunitrazepam contained within the sample is simultaneously hydrolyzed and reduced to a hydrolyzed and reduced species by addition to the sample of a hydrolyzing agent and a reducing agent. The preferred reducing agent is tin (II) chloride. The preferred hydrolyzing agent is hydrochloric acid.

The reducing agent and hydrolyzing agent are provided in amounts to effectively reduce and hydrolyze flunitrazepam in the sample to the reduced and hydrolyzed species in an amount sufficient to provide a concentration of reduced and hydrolyzed species capable of being calorimetrically detected following Schiff base formation with a visualizing agent. Suitable visualizing compounds may be 4-dimethylaminocinnamaldehyde or 4-dimethylaminobenzaldehyde. The colorimetric indication is preferably visible to the naked eye of one practicing the invention as the invention is useful as a method practiced in the field by the general public, where no complex analytical steps are required or possible.

Other features and advantages of this invention will become clear to the reader after careful consideration is given to the following detailed description of the preferred exemplary embodiments thereof

DETAILED DESCRIPTION OF THE INVENTION

It was previously known in the field that certain benzodiazepines may be detected using a procedure requiring the hydrolysis of those benzodiazepines to the corresponding 2-aminobenzophenones. See Laudszun and Kovar (Pharm. Acta Helv. 66, 268 (1991)). Scheme 1 below illustrates the previously-known reaction with a general benzodiazepine (1) being hydrolyzed to a 2-aminobenzophenone (2) in the presence of hydrochloric acid and heat.

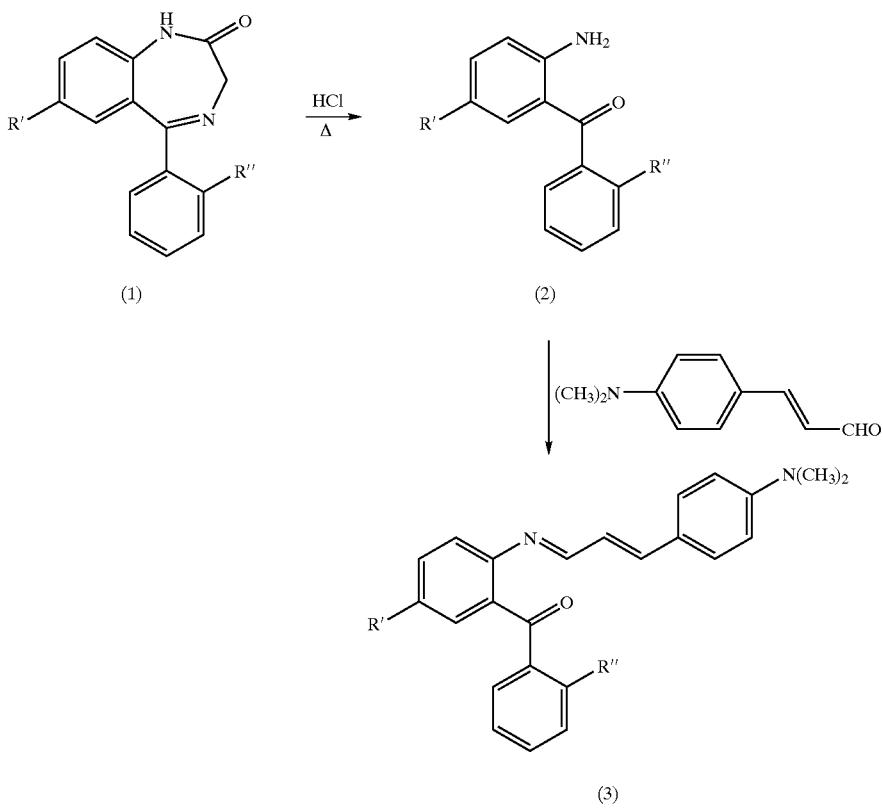

Scheme 1 further illustrates the resulting 2-aminobenzophenone (2) being subsequently reacted with a conjugated aldehyde to yield a highly conjugated colored species (3). Specifically, the highly conjugated colored species (3) is formed via Schiff base formation between the 2-aminobenzophenone (2) and conjugated aldehyde 4-dimethylaminocinnamaldehyde.

However, Scheme 1 shown above is understood to have certain limitations. Scheme 2 below illustrates that the detection method of Scheme 1 is incapable of detecting particular species of benzodiazepines, most notably flunitrazepam.

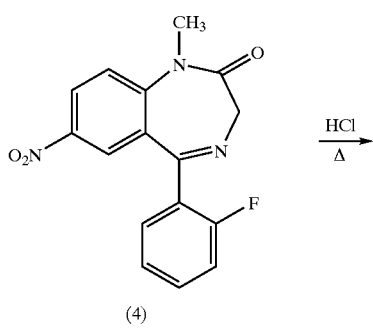

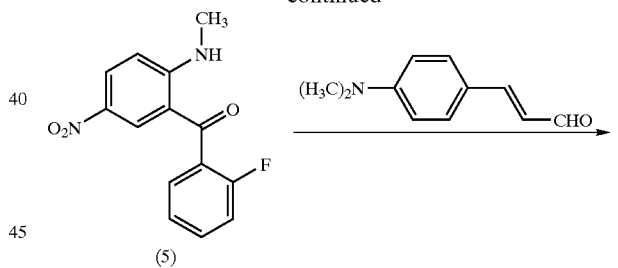

The reason for the ineffectiveness of the above-described test for flunitrazepam is believed due to the presence of a nitro group at position 5 of the aminobenzophenone (5) resulting from hydrolysis of flunitrazepam (4). The nitro group is believed to reduce the nucleophilicity of the amino group located para to the nitro group due to the nitro group's strong electron drawing effects. Therefore, it is widely held that the hydrolyzed form (5) of flunitrazepam cannot form corresponding color compounds by the reactions shown in Scheme 1. Based upon the preceding rationale, the procedure shown in Scheme 1 is most likely ineffective in detecting all benzodiazepine species having electron withdrawing groups located at the para and presumably ortho positions relative to the respective amino group.

The present invention provides an improvement over the previous method of Scheme 1 by reducing or eliminating the electron withdrawing effects of the nitro group at the 7-position of flunitrazepam (4) thereby providing a benzophenone product (6) capable of undergoing Schiff base formation with a visualizing compound such as 4-dimethylaminocinnamaldehyde to form a colored species (7). According to the invention, the nitro group is reduced to a hydroxylamino or amino functionality simultaneously with hydrolysis of the flunitrazepam and prior to addition of the visualizing compound. Scheme 3 below illustrates an exemplary chemical reaction according to the invention wherein flunitrazepam is simultaneously hydrolyzed by contact with a hydrolyzing agent such as dilute hydrochloric acid and reduced to a reduced species by contact with a reducing agent such as tin (II) chloride.

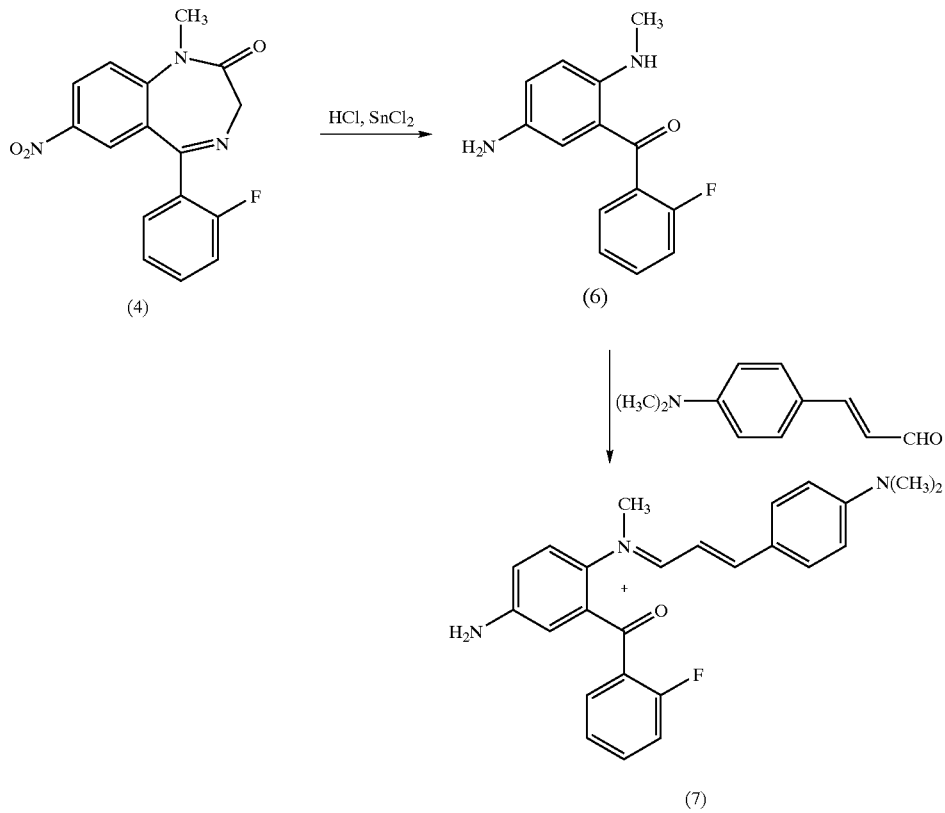

A method according to the invention may be carried out on a wide range of samples suspected of containing flunitrazepam. The sample may be a liquid and more specifically a beverage of some type. As shown in the examples set forth below, the present invention is effective where beverages contain ethanol as well as other constituents that traditionally make up drinks served on a social basis. In addition to detecting flunitrazepam, the present invention may be useful in the detection of nitrazepam and clonazepam, structurally-similar benzodiazepines bearing a nitro group at the 7-position.

A suitable reducing agent may be any active metal or other reducing agent known in the art to be capable of reducing the nitro group of flunitrazepam to a reduced species. Suitable active metals include zinc, tin, magnesium, iron, cobalt, copper, bismuth, lead or indium. This list is meant to be illustrative and other active metals may be suitable for use with the invention. The preferred reducing agent of the present invention is tin (II) chloride. Alternatively, reducing agents such as alkaline sodium hydrosulfite (sodium dithionite), sodium borohydride, or ammoniacal ferrous sulfate may be utilized with the present invention. Other reducing agents not specifically set forth here capable of effectively reducing flunitrazepam may also be useful in the present method. However, not all reducing agents are suitable with the method as sodium sulfite and sodium thiosulfate have been identified as not suitable for use with the invention.

The reducing agent and hydrolyzing agent are provided in the invention at concentrations to effectively reduce and hydrolyze flunitrazepam in the sample to the reduced and hydrolyzed species in an amount sufficient to provide a concentration of reduced and hydrolyzed species capable of being colorimetrically detected following Schiff base formation with a visualizing agent. For tin (II) chloride, the concentration to provide this effective reduction may be as low as 0.75% with 2.5% being the preferred final concentration ("final concentration", unless specifically noted otherwise, is defined herein as the concentration prior to addition of the visualizing agent).

Zinc may also be used as a reducing agent with the present invention and provides an effective reduction of flunitrazepam for use in combination with the visualizing agents disclosed below. Zinc final concentration (prior to addition of the visualizing agent) may be as low as 0.04% with 0.4% being the preferred concentration of zinc necessary to carry out an effective reduction of flunitrazepam.

A hydrolyzing agent suitable for use with the invention may be hydrochloric acid.

Experimentation has demonstrated that nitric and sulfuric acids are not suitable for use with the invention. Although hydrobromic acid, hydroiodic acid and hydrofluoric acid have each been demonstrated or are presumed to have some use as hydrolyzing agents, their hazardous natures and/or high costs rule out their use as safe, practical hydrolyzing agents for use with the invention. Phosphoric acid and acetic acid have also been demonstrated to hydrolyze flunitrazepam, but heating to reflux is required. The final concentration of hydrochloric acid necessary to carry out the effective hydrolysis of flunitrazepam may be from about 0.2% up to 18.5% with the preferred final concentration being about 2.0%.

Following the formation of the reduced and hydrolyzed benzophenone species corresponding to flunitrazepam, the reduced and hydrolyzed species is chemically converted to a Schiff base by the addition of the visualizing compound, generally an aldehyde and in particular 4-dimethylaminocinnamaldehyde or 4-dimethylaminobenzaldehyde. 4-dimethylaminocinnamaldehyde is the preferred visualizing agent and can be used at concentrations as low as about 0.1% up to about 0.5% (concentration after addition to reduced and hydrolyzed species). Higher concentrations are not suitable as 4-dimethylaminocinnamaldehyde is difficult to maintain in solution above about 1.0%. Stock solutions of these two compounds are made in 95% ethanol. The preferred concentration of this reagent is about 0.125% to about 0.25% with 0.125% being most preferred. 4-dimethylaminobenzaldehyde may also be a suitable visualizing agent. This alternate visualizing agent may be used in a concentration range of about 0.05% up to about 0.5%, with 0.25% being preferred. Stock solutions of the visualizing agents noted above are typically prepared and maintained in 95% ethanol prior to use.

The reduction and hydrolysis steps are preferably carried out at ambient temperature. Room temperatures in the range of 15° C. to 25° C. are most preferred, although temperatures up to 100° C. are also effective and may further accelerate the already rapid conversion to a reduced and hydrolyzed species. Ambient temperature is preferred as a user in the field may not have access to a heat source. The time necessary for effective reduction and hydrolysis for the preferred embodiment disclosed herein (2.5% final concentration tin (II) chloride and 2.0% final concentration HCl) is in the range of about 15 seconds for flunitrazepam concentrations in the range of 1000 ppm. This time period is approximately 2.0 to 2.5 minutes for flunitrazepam concentrations in the range of 100 ppm. Finally, a time period of approximately 5.0 to 10.0 minutes is necessary for effective reduction and hydrolysis of flunitrazepam in the range of 10 ppm. These times represent reduction and hydrolysis times and do not include the time necessary for the formation of colored Schiff base species upon addition of the visualizing agent. However, the visualizing agents used in the present invention were found to provide an immediate unambiguous color reaction which intensified with the passage of time.

The method according to the preferred embodiment set forth above has been shown capable of reliably detecting flunitrazepam in a sample at a concentration of 10 ppm. The maximum detectable amount of flunitrazepam appears to be only bounded by the maximum solubility of flunitrazepam in aqueous or aqueous/ethanol solutions. Although 10 ppm of flunitrazepam is, in fact, detectable by the present invention, it is believed that 10 ppm is well below the typical dosage of flunitrazepam useful in illicit activities. Flunitrazepam is typically supplied in 1 milligram (mg) or 2 mg tablets. Ingestion of a 1 mg ROHYPNOL tablet is known in the field to impair cognitive and psychomotor functions. However, a higher dosage appears necessary to bring on total incapacity. If a 1 mg tablet is dissolved in a 100 mL drink, the resulting concentration is approximately 10 ppm. However, it is reasonable to assume that assailants may regularly use much higher concentrations in hopes of successfully carrying out their assaults without the later chance of identification by the victim. The present invention is therefore useful for qualitatively detecting flunitrazepam in concentrations likely to be encountered under real conditions in the field.

How to make and use the invention is further illustrated by the following examples.

EXAMPLE 1

A 0.1% solution of flunitrazepam dissolved in water was prepared and 10 drops of this solution was added to 10 drops of 4% hydrochloric acid and the mixture was heated to a boil for a few seconds. In this and all following examples, one drop is approximately 0.02 mL. Immediately following boiling, approximately 1.5 mg of powdered zinc and approximately 2 mg of ammonium chloride were added to the reaction. The mixture was again boiled for a few seconds and allowed to cool to ambient temperature. Upon cooling, 25 drops of a 0.1% aqueous solution of 4-dimethylaminocinnamaldehyde was added to the reduced and hydrolyzed mixture. A pinkish-red color immediately developed. A blank tube containing only water did not develop this color.

EXAMPLE 2

A solution was prepared by dissolving 0.1 g of 4-dimethylaminocinnamaldehyde in 9.9 g of 95% ethanol. A separate solution containing 0.5 g tin (II) chloride dihydrate in 9.5 g of approximately 4% HCl (aqueous) was also prepared. The solution containing the tin (II) chloride and the HCl was intended to serve the dual role of hydrolyzing the flunitrazepam and reducing the nitro group present in flunitrazepam to a reduced functionality. In addition, a 0.1% (1000 ppm) standard solution containing 0.103 g flunitrazepam dissolved in 9.90 g 47.5% ethanol was also prepared. From this standard solution, standard dilutions were prepared at 0.01% (100 ppm) and 0.001% (10 ppm).

In this and all examples contained herein, the 4-dimethylaminocinnamaldehyde, 4-dimethylaminobenzaldehyde and sodium borohydride were obtained from Aldrich Chemical Company. Flunitrazepam was purchased from Sigma Chemical under U.S. Department of Justice Drug Enforcement Administration licensing, as mandated by the Controlled Substances Act of 1970. Tin (II) chloride was obtained from Fisher Scientific Company, hydrochloric acid was from J. T. Baker, Inc. Other reagents, mentioned in additional examples, and their suppliers, include the elements Co, Cu, Mg, Fe, Bi, In and the compound $FeSO_4$, all from Fisher Scientific. Elemental Sn and Pb were obtained from Sargent Welch. Ammonium hydroxide was obtained from J. T. Baker, 95% ethanol was obtained from David Sherman Corporation, St. Louis, Mo. under the registered trademark EVERCLEAR.

To each of four polypropylene snap cap tubes was added 10 drops of the tin (II) chloride solution. To one tube was added 10 drops of 47.5% ethanol to serve as a blank. The second through fourth tubes received, respectively, 10 drops of 0.001%, 0.01%, and 0.1% flunitrazepam as prepared above. The tubes were securely closed, gently mixed by inversion, and allowed to stand for 5 minutes. At the end of this time period, 25 drops of the 4-dimethylaminocinnamaldehyde solution as prepared above was added to each of the tubes. Tubes were inverted and examined immediately for color changes. The blank was initially pale yellow in color and remained yellow in color upon standing. The 0.001% flunitrazepam-containing tube turned from pale yellow to orange in color. The 0.01% flunitrazepam-containing tube turned from pale yellow to a bright pink color. The 0.1% flunitrazepam-containing tube turned from pale yellow to a deep cherry red color.

The above-described experimental was repeated with the standard solution of flunitrazepam absent ethanol. The serial dilutions were prepared and the experiment was repeated as described above with similar results being obtained. All of the colored indications appeared a bit less intense but still yielded unambiguous colorimetric indications of the presence of flunitrazepam. This example illustrates the general usefulness of the present invention for detecting flunitrazepam in aqueous samples and aqueous/alcohol mixtures.

EXAMPLE 3

An experiment was carried out to further identify parameters of the present invention. Table 1 illustrates data obtained for various combinations of reducing/hydrolyzing agents and visualizing agents (color reagents) for the detection of 10 to 1000 ppm flunitrazepam in aqueous and aqueous/alcohol samples.

Unless indicated otherwise in this example (see notes below Table 1 for hydrosulfite, sulfite, thiosulfate, aluminum and ferrous sulfate-related experimentals), the experimental described in Example 2 was substantially followed. Briefly, the reducing/hydrolyzing agents were prepared having initial concentrations (prior to addition of the test mixture, or sample, in column 1) as indicated in column 2 of Table 1. Test mixtures were prepared to initial concentrations (prior to addition of the reducing/hydrolyzing agent in column 2) as indicated in column 1 below. Unless noted otherwise, 10 drops of the reducing/hydrolyzing agents were added to polypropylene snap cap tubes. Subsequently, 10 drops of the test mixtures were added to each respective tube. The tubes were securely closed, gently mixed by inversion, and allowed to stand for 5 minutes as indicated in column 4 of Table 1. Subsequently, 25 drops of the visualizing agent (color reagent; prepared as noted below Table 1) indicated in column 3 was added to each of the tubes. Column 3 indicates the initial concentration of the visualizing agent prior to addition to the tubes. The tubes were immediately examined for any color change and final test mix colors were recorded and are shown in column 6 of Table 1.

Corresponding blanks were prepared for each test mixture and the final colors of the respective blanks are described in Column 5 of Table 1.

TABLE 1

| Test Mixture | Reducing/ Hydrolyzing Rgts | Color Reagent | Reaction Time | Blank Color | Test Mix Color |
| --- | --- | --- | --- | --- | --- |
| 100 ppm Flunitrazepam; 47.5% EtOH | 5% $SnCl_2$, 4% HCl | 0.25% 4-DMAC* | 5.0 minutes | Yellow | Pinkish-orange |
| 10 ppm Flunitrazepam; 47.5% EtOH | 5% $SnCl_2$, 4% HCl | 0.25% 4-DMAC* | 5.0 minutes | Yellow | Orangish yellow |
| 100 ppm Flunitrazepam; 47.5% EtOH | 5% $SnCl_2$, 37% HCl | 0.25% 4-DMAC* | 0.5 minute | Yellow | Intense Pink |
| 100 ppm Flunitrazepam; 47.5% EtOH | 37% HCl | 0.25% 4-DMAC* | 5.0 minutes | Pale yellow | Pale yellow |
| 100 ppm Flunitrazepam 47.5% EtOH | 5% $SnCl_2$, | 0.25% 4-DMAC* | 5.0 minutes | Yellow | Orangish yellow |
| 100 ppm Flunitrazepam; 47.5% EtOH | 5% $SnCl_2$, 37% HCl | 0.25% 4-DMAC* | 5.0 minutes | Pale Yellow | Pink |
| 100 ppm Flunitrazepam; 47.% EtOH | 5% $SnCl_2$, 37% HCl | 1.00% 4-DMAC** | 5.0 minutes | Colorless | Intense yellow |
| 10 ppm Flunitrazepam; 47.5% EtOH | 5% $SnCl_2$, 4% HCl | 1.00% 4-DMAB** | 5.0 minutes | Colorless | Pale yellow |
| 1000 ppm Flunitrazepam; Water | 5% $SnCl_2$, 4% HCl | 0.25% 4-DMAC* | 5.0 minutes | Yellow | Pink |
| 100 ppm Flunitrazepam; Water | 5% $SnCl_2$, 4% HCl | 0.25% 4-DMAC* | 5.0 minutes | Yellow | Orange-yellow |
| 10 ppm Flunitrazepam; Water | 5% $SnCl_2$, 4% HCl | 0.25% 4-DMAC* | 5.0 minutes | Yellow | Yellow |
| 1000 ppm Flunitrazepam; Water | 5% $SnCl_2$, 4% HCl | 1.00% 4-DMAB** | 5.0 minutes | Colorless | Yellow |
| 100 ppm Flunitrazepam; Water | 5% $SnCl_2$, 4% HCl | 1.00% 4-DMAB** | 5.0 minutes | Colorless | Pale Yellow |
| 10 ppm Flunitrazepam; Water | 5% $SnCl_2$, 4% HCl | 1.00% 4-DMAB** | 5.0 minutes | Colorless | Very Pale Yellow |

TABLE 1-continued

| Test Mixture | Reducing/ Hydrolyzing Rgts | Color Reagent | Reaction Time | Blank Color | Test Mix Color |
|---|---|---|---|---|---|
| 100 ppm Flunitrazepam; 47.5% ethanol | $Na_2S_2O_4$***, $NH_4OH$, HCl | 0.25% 4-DMAC* | 5.0 minutes | Yellow | Red |
| 100 ppm Flunitrazepam; 47.5% ethanol | $Na_2SO_3$***, $NH_4OH$, HCl | 0.25% 4-DMAC* | 5.0 minutes | Yellow | Yellow |
| 100 ppm Flunitrazepam; 47.5% ethanol | $Na_2S_2O_3$***, $NH_4OH$, HCl | 0.25% 4-DMAC* | 5.0 minutes | Yellow | Yellow |
| 100 ppm Flunitrazepam; 47.5% ethanol | Al (10 mg), 4% HCl (10 drops) | 0.25% 4-DMAC* | 5.0 minutes | Yellow | Yellow |
| 100 ppm Flunitrazepam; 47.5% ethanol | Al (10 mg) ****NaOH, HCl | 0.25% 4-DMAC* | 5.0 minutes | Yellow | Intense Pink |
| 100 ppm Flunitrazepam; 47.5% ethanol | $FeSO_4$,***** $NH_4OH$, HCl | 0.25% 4-DMAC* | 5.0 minutes | Yellow | Pink |
| 100 ppm Flunitrazepam; 47.5% ethanol | Mg (10 mg), 4% HCl (10 drops) | 0.25% 4-DMAC* | 5.0 minutes | Yellow | Pink Orange |
| 100 ppm Flunitrazepam; 47.5% ethanol | Sn (10 mg), 4% HCl (10 drops) | 0.25% 4-DMAC* | 5.0 minutes | Yellow | Pale Orange |
| 100 ppm Flunitrazepam; 47.5% ethanol | In (18 mg), 4% HCl (10 drops) | 0.25% 4-DMAC* | 5.0 minutes | Yellow | Red Orange |
| 100 ppm Flunitrazepam; 47.5% ethanol | Pb (11 mg), 4% HCl (10 drops) | 0.25% 4-DMAC* | 5.0 minutes | Yellow | Pink Orange |
| 100 ppm Flunitrazepam; 47.5% ethanol | Bi (10 mg), 4% HCl (10 drops) | 0.25% 4-DMAC* | 5.0 minutes | Yellow | Pink |
| 100 ppm Flunitrazepam; 47.5% ethanol | Fe (8 mg), 4% HCl (10 drops) | 0.25% 4-DMAC* | 5.0 minutes | Yellow | Pink Orange |
| 100 ppm Flunitrazepam; 47.5% ethanol | Co (11 mg), 4% HCl (10 drops) | 0.25% 4-DMAC* | 5.0 minutes | Yellow | Cherry Red |
| 100 ppm Flunitrazepam; 47.5% ethanol | Cu (10 mg), 4% HCl (10 drops) | 0.25% 4-DMAC* | 5.0 minutes | Yellow | Pink Orange |

*DMAC = 4-dimethylaminocinnamaldehyde (in 95% ethanol)
**DMAB = 4-dimethylaminobenzaldehyde (in 95% ethanol)
***Each of the sulfur reducing agents (hydrosulfite, sulfite and thiosulfate) was added in a 10 mg quantity to 10 drops of the test mixture, followed by the addition of 5 drops of concentrated $NH_4OH$. After 5 minutes, 5 drops of concentrated HCl was added. After an additional minute post HCl addition, the color reagent (DMAC, 25 drops) was added.
****Al (10 mg) was added to 10 drops of the test mixture, followed by the addition of 5 drops 2.5N NaOH solution. After 5 minutes, 5 drops of concentrated HCl were carefully and slowly added. After an additional minute, 25 drops of DMAC solution were added.
*****$FeSO_4$ (10 mg) was added to the test mixture, followed by 5 drops of concentrated $NH_4OH$. A dark green precipitate formed. After 5 minutes, 5 drops of concentrated HCl were added. The precipitate dissolved to give a yellow solution. After an additional minute, the 25 drops of DMAC solution were added to develop the color.

The data presented in Table 1 illustrate the various combinations of chemicals potentially useful in practicing the present invention. In particular, the preferred combination of tin (II) chloride/dilute HCl and 4-dimethylaminocinnamaldehyde demonstrates particular usefulness in detecting flunitrazepam in ethanol-containing samples.

EXAMPLE 4

This example illustrates the usefulness of the preferred embodiment of the invention for detecting flunitrazepam in alcoholic beverages commonly encountered in social situations. The reducing/hydrolyzing agent was prepared with initial concentrations of 5% tin (II) chloride and 4% HCl. The visualizing agent was 0.25% dimethylaminocinnamaldehyde in 95% ethanol. Ten drops of the reducing/hydrolyzing agent was placed in a polypropylene tube and 10 drops of the sample in Column 1 of Table 2 was added to the tube. The contents were mixed and allowed to stand for 5 minutes. Twenty five drops of the visualizing agent was then added to the contents of the tube, gently mixed, and any color changes were noted and recorded in Column 3 of Table 2.

Column 1 of Table 2 lists the beverages tested. The respective recipes for preparing those beverages are located immediately below Table 2 with the source of each ingredient being noted. Each of the respective beverages was spiked with flunitrazepam to a concentration of 100 ppm. Corresponding blank beverages were also prepared not containing flunitrazepam. Column 2 indicates the final color of the blank samples immediately after addition of the visualizing agent. Column 3 shows the final color of the samples spiked with flunitrazepam immediately following addition of the visualizing agent and upon standing for an extended period of time (approximately 10 to 15 minutes).

| Beverage | Blank Color | 0.01% Flunitrazepam Color |
|---|---|---|
| Bourbon | Yellow | Orange Pink - Pink on Standing |
| Gin | Yellow | Orange Pink - Pink on Standing |
| Scotch | Yellow | Orange Pink - Pink on Standing |
| Tequila | Yellow | Orange Pink - Pink on Standing |
| Bloody Mary | Yellow | Orange Pink - Pink on Standing |
| Cosmopolitan | Yellow | Orange Pink - Pink on Standing |
| Mai Tai | Yellow | Yellow - Pink on Standing |
| Tequila Sunrise | Pale Orange | Pink (takes 5 min to develop) |
| White Russian | Yellow Orange | Orange Pink - Pink on Standing |
| Classic Coca Cola | Yellow | Orange |

Drink Recipes Used in the Above Study
Bloody Mary:
  3.0 mL vodka available under the trademark SMIRNOFF'S
  6.0 mL tomato juice available under the trademark CAMPBELL'S
  1.0 mL lemon juice available under the trademark REALEMON
Cosmopolitan:
  1.0 mL triple-sec liquor available under the trademark HIRAM WALKER
  2.0 mL cranberry juice available under the trademark OCEAN SPRAY
  1.0 mL lemon juice available under the trademark REALEMON
  3.0 mL vodka available under the trademark SMIRNOFF'S
Mai Tai:
  4.0 mL mai tai tropical cocktail mix available under the trademark HOLLAND HOUSE
  4.0 mL dark rum available under the trademark MEYER'S
  2.0 mL water
Tequila Sunrise:
  2.0 mL grenadine syrup available under the trademark COLLINS
  10.0 mL orange juice available under the trademark JEWEL
  2.0 mL arundas tequila available under the trademark HIRAM WALKER
  5.0 mL water
White Russian:
  3.0 mL vodka available under the trademark SMIRNOFF'S
  2.0 mL kahlua liquor available under the trademark KAHLUA
  6.0 mL milk available under the trademark JEWEL
  2.0 mL water
Bourbon whiskey was available under the trademark MAKER'S MARK. Scotch whiskey was available under the trademark THE CHICAGO CLUB. Gin was available under the trademark CALVERT.

This example shows the usefulness of a method according to the invention for the qualitative determination of flunitrazepam in a sample, particularly an alcoholic beverage as encountered in the field.

While the invention has been described with reference to preferred embodiments, those skilled in the art will appreciate that certain substitutions, alterations, and omissions may be made without departing from the spirit of the invention. Accordingly, the foregoing description is meant to be exemplary only and should not limit the scope of the invention set forth in the following claims.

What is claimed is:

1. A method for detecting the presence of flunitrazepam in a sample, comprising the steps of:
  obtaining a sample suspected to contain flunitrazepam;
  simultaneously reducing and hydrolyzing flunitrazepam contained within the sample to a reduced and hydrolyzed species by the addition of a hydrolyzing agent and a reducing agent to the sample; and
  adding a visualizing agent to the sample which chemically reacts with the reduced and hydrolyzed species of the flunitrazepam to provide a colorimetric indication of the presence of flunitrazepam within the sample.

2. A method according to claim 1 wherein the sample suspected of containing flunitrazepam is a liquid.

3. A method according to claim 2 wherein the liquid contains ethanol in addition to any suspected flunitrazepam.

4. A method according to claim 1 wherein the reducing agent and hydrolyzing agent are provided at concentrations to effectively reduce and hydrolyze flunitrazepam in the sample to the reduced and hydrolyzed species in an amount sufficient to provide a concentration of reduced and hydrolyzed species capable of being calorimetrically detected following Schiff base formation with the visualizing agent wherein the flunitrazepam is present in the sample at a concentration of about 10 ppm or greater.

5. A method according to claim 1 wherein the reducing agent is zinc.

6. A method according to claim 5 wherein the hydrolyzing agent is hydrochloric acid and the hydrochloric acid is added to a final concentration of at least 0.2% and the zinc is added to a final concentration of at least 0.4%.

7. A method according to claim 6 wherein the hydrochloric acid is added to a final concentration of about 2.0% and the zinc is added to a final concentration of about 0.4%.

8. A method according to claim 6 wherein the simultaneous reducing and hydrolyzing step is performed at a temperature of from ambient temperature up to 100° C.

9. A method according to claim 6 wherein the temperature at which the simultaneous reducing and hydrolyzing step is performed is ambient temperature.

10. A method according to claim 1 wherein the simultaneous reducing and hydrolyzing step is performed at a temperature of from ambient temperature up to 100° C.

11. A method according to claim 1 wherein the temperature the simultaneous reducing and hydrolyzing step is performed at ambient temperature.

12. A method according to claim 1 wherein the reducing agent is tin (II) chloride.

13. A method according to claim 12 wherein the hydrolyzing agent is hydrochloric acid and the hydrochloric acid is added to a final concentration of at least 0.2% and the tin (II) chloride is added to a final concentration of at least 0.75%.

14. A method according to claim 13 wherein the hydrochloric acid is added to a final concentration of about 2.0% and the tin (II) chloride is added to a final concentration of about 2.5%.

15. A method according to claim 13 wherein the simultaneous reducing and hydrolyzing step is performed at ambient temperature up to 100° C.

16. A method according to claim 13 wherein the simultaneous reducing and hydrolyzing step is carried out at ambient temperature.

17. A method according to claim 1 wherein the visualizing agent is 4-dimethylaminobenzaldehyde.

18. A method according to claim 17 wherein the 4-dimethylaminobenzaldehyde is added to the reduced and hydrolyzed species to a concentration of at least 0.05%.

19. A method according to claim 17 wherein the 4-dimethylaminobenzaldehyde is added to the reduced and hydrolyzed species to a concentration of about 0.25%.

20. A method according to claim 1 wherein the visualizing agent is 4-dimethylaminocinnamaldehyde.

21. A method according to claim 20 wherein the 4-dimethylaminocinnamaldehyde is added to the reduced and hydrolyzed species to a concentration of at least 0.125%.

22. A method according to claim 20 wherein the 4-dimethylaminocinnamaldehyde is added to the reduced and hydrolyzed species to a concentration of about 0.125%.

23. A method according to claim 1 wherein the hydrolyzing agent is hydrochloric acid.

24. A method according to claim 1 wherein the reducing agent is selected from the group consisting of zinc, tin, magnesium, iron, cobalt, copper, bismuth, lead and indium.

25. A method for detecting the presence of flunitrazepam in a sample, comprising the steps of:

obtaining a sample suspected to contain flunitrazepam;

reducing the flunitrazepam contained within the sample to a reduced species by the addition of a reducing agent to the sample;

hydrolyzing the flunitrazepam contained within the sample to a hydrolyzed species by addition of a hydrolyzing agent to the sample; and adding a visualizing agent to the sample which chemically reacts with the both reduced and hydrolyzed species of the flunitrazepam to provide a colorimetric indication of the presence of flunitrazepam within the sample.

26. A method according to claim 25 wherein the reducing agent and hydrolyzing agent are provided at concentrations to effectively reduce and hydrolyze flunitrazepam in the sample to the reduced and hydrolyzed species in an amount sufficient to provide a concentration of reduced and hydrolyzed species capable of being calorimetrically detected following Schiff base formation with the visualizing agent wherein the flunitrazepam is present in the sample at a concentration of about 10 ppm or greater.

27. A method according to claim 25 wherein the reducing and hydrolyzing steps are carried out at ambient temperature.

28. A method according to claim 25 wherein the reducing agent is selected from the group consisting of zinc, tin, magnesium, iron, cobalt, copper, bismuth, lead and indium.

29. A method according to claim 25 wherein the hydrolyzing agent is hydrochloric acid.

30. A method for detecting the presence of flunitrazepam in a sample, comprising the steps of:

obtaining a sample suspected to contain flunitrazepam;

reducing and hydrolyzing flunitrazepam contained within the sample to a reduced and hydrolyzed species; and adding a visualizing agent to the sample which chemically reacts with the reduced and hydrolyzed species of the flunitrazepam to provide a colorimetric indication of the presence of flunitrazepam within the sample.

31. A method for detecting the presence of flunitrazepam in a sample, comprising the steps of:

obtaining a sample suspected to contain flunitrazepam;

simultaneously reducing and hydrolyzing flunitrazepam contained within the sample to a reduced and hydrolyzed species by the addition of a hydrolyzing agent and a reducing agent to the sample wherein the simultaneous reducing and hydrolyzing is carried out at ambient temperature, the hydrolyzing agent is hydrochloric acid, and the reducing agent is zinc, tin, magnesium, iron, cobalt, copper, bismuth, lead or indium; and subsequently adding a visualizing agent to the sample which chemically reacts with the reduced and hydrolyzed species of the flunitrazepam to provide a colorimetric indication of the presence of flunitrazepam within the sample, wherein the reducing agent and hydrolyzing agent are provided at concentrations to effectively reduce and hydrolyze flunitrazepam in the sample to the reduced and hydrolyzed species in an amount sufficient to provide a concentration of reduced and hydrolyzed species capable of being calorimetrically detected following Schiff base formation with the visualizing agent wherein the flunitrazepam is present in the sample at a concentration of about 10 ppm or greater.

* * * * *